United States Patent
Jacobson-Shagan

(10) Patent No.: US 9,855,121 B2
(45) Date of Patent: Jan. 2, 2018

(54) METHOD AND APPARATUS FOR PREPARING CONTOURED GLAZED COMPOSITE DENTAL VENEERS

(71) Applicant: Dental Art Innovations, LLC, San Diego, CA (US)

(72) Inventor: Sigal Jacobson-Shagan, San Diego, CA (US)

(73) Assignee: Dental Art Innovations, LLC, San Diego, CA (US)

(*) Notice: Subject to any disclaimer, the term of this patent is extended or adjusted under 35 U.S.C. 154(b) by 98 days.

(21) Appl. No.: 14/741,313

(22) Filed: Jun. 16, 2015

(65) Prior Publication Data

US 2015/0282906 A1 Oct. 8, 2015

Related U.S. Application Data

(63) Continuation-in-part of application No. PCT/AU2012/001575, filed on Dec. 20, 2012.

(51) Int. Cl.
*A61C 13/08* (2006.01)
*A61C 13/00* (2006.01)
(Continued)

(52) U.S. Cl.
CPC .............. *A61C 13/082* (2013.01); *A61C 5/20* (2017.02); *A61C 5/85* (2017.02); *A61C 13/0003* (2013.01); *A61C 19/004* (2013.01)

(58) Field of Classification Search
CPC . A61C 13/0001; A61C 13/0003; A61C 13/08; A61C 13/081; A61C 13/082;
(Continued)

(56) References Cited

U.S. PATENT DOCUMENTS 1,265,022 A * 5/1918 Zurbrigg ................ A61C 13/26
433/191
1,265,581 A * 5/1918 Zurbrigg ................ A61C 5/125
433/39
(Continued)

FOREIGN PATENT DOCUMENTS

DE 6918934 10/1969
EP 0079299 5/1983
(Continued)

OTHER PUBLICATIONS

Uveneer website. <http://uveneer.com/uveneer/>. Accessed Feb. 8, 2017.*
(Continued)

*Primary Examiner* — Eugene T Wu
(74) *Attorney, Agent, or Firm* — TraskBritt

(57) ABSTRACT

Disclosed is a template for forming a veneer on a tooth using a composite resin material that is curable by radiation. The template includes a tooth-contacting portion having a smooth concave surface for contacting the composite, the smooth concave surface having a shape that is complementary to a desired natural tooth shape. The tooth-contacting portion is formed of a material capable of transmitting the radiation such that the composite is curable through the tooth-contacting portion to form a veneer having a surface shape that conforms to the desired natural tooth shape. Also disclosed is a kit including a plurality of such templates and a method of using the templates to form a veneer.

17 Claims, 6 Drawing Sheets

(51) Int. Cl.
*A61C 13/15* (2006.01)
*A61C 5/20* (2017.01)
*A61C 5/85* (2017.01)

(58) Field of Classification Search
CPC ....... A61C 13/087; A61C 13/09; A61C 13/12;
A61C 13/14; A61C 13/16; A61C 13/18;
A61C 13/20; A61C 5/002; A61C 5/125;
A61C 5/12; A61C 5/14
See application file for complete search history.

(56) References Cited

U.S. PATENT DOCUMENTS

| | | | |
|---|---|---|---|
| 2,629,172 A * | 2/1953 | Keiger | A61C 5/00 433/40 |
| 4,129,946 A * | 12/1978 | Kennedy | A61C 5/10 433/37 |
| 4,449,928 A * | 5/1984 | von Weissenfluh | A61C 5/04 433/229 |
| 4,500,288 A * | 2/1985 | von Weissenfluh | A61C 5/00 433/226 |
| 4,822,278 A | 4/1989 | Oliva et al. | |
| 5,104,591 A | 4/1992 | Masuhara et al. | |
| 5,114,341 A * | 5/1992 | Kassel | A61C 5/125 433/39 |
| 5,195,889 A * | 3/1993 | von Weissenfluh | A61C 5/125 433/40 |
| 5,415,543 A | 5/1995 | Rozmajzl, Jr. | |
| 5,759,032 A * | 6/1998 | Bartel | A61C 19/004 385/43 |
| 6,257,885 B1 * | 7/2001 | Safstrom | A61C 3/08 433/215 |
| 6,659,772 B2 * | 12/2003 | Margeas | A61C 5/00 433/215 |
| 7,442,040 B2 | 10/2008 | Kuo | |
| 8,002,546 B2 | 8/2011 | Viscomi | |
| 2004/0214130 A1 | 10/2004 | Fischer et al. | |
| 2008/0081318 A1 * | 4/2008 | Fischer | A61C 13/082 433/222.1 |
| 2008/0131845 A1 * | 6/2008 | Viscomi | A61C 5/002 433/217.1 |
| 2008/0299510 A1 * | 12/2008 | Penchas | A61C 5/00 433/34 |
| 2009/0155741 A1 | 6/2009 | Viscomi | |

FOREIGN PATENT DOCUMENTS

| | | | |
|---|---|---|---|
| EP | 0087022 | 8/1983 | |
| EP | 0087022 A1 * | 8/1983 | ............ A61C 5/00 |

OTHER PUBLICATIONS

International Search Report; PCT/AU2012/001575 dated Feb. 7, 2013.
International Written Opinion for International Application No. PCT/AU2012/001575, dated Feb. 7, 2013, 4 pages.
Levin, Edwin I., "Removable Prosthodontics: Dental esthetics and the golden proportion", The Journal of Prosthetic Dentistry, vol. 40(3), (Sep. 1978), pp. 244-252.
Preston, Jack D., "The Golden Proportion Revisited", Journal of Esthetic Dentistry, vol. 5(6), (1993), pp. 247-251.
Snow, Stephen R., "Esthetic Smile Analysis of Maxillary Anterior Tooth Width: The Golden Percentage", Journal of Esthetic Denistry, vol. 11(4), (1999), pp. 177-184.
Ward, Daniel H., "A Study of Dentists' Preferred Maxillary Anterior Tooth Width Proportions: Comparing the Recurring Esthetic Dental Proportion to Other Mathematical and Naturally Occurring Proportions", J. Esthet. Restor. Dent., vol. 19(6), (Nov. 2007), pp. 324-339.
Wheele's Dental Anatomy, Physiology and Occlusion (7th edition, W.B. Saunders, 1993) 4 pages.

\* cited by examiner

METHOD AND APPARATUS FOR PREPARING CONTOURED GLAZED COMPOSITE DENTAL VENEERS

CROSS-REFERENCE TO RELATED APPLICATION

This application is a continuation-in-part of co-pending International Patent Application PCT/AU2012/001575, filed Dec. 20, 2012, designating the United States, published in English as International Patent Publication WO 2014/094030 A1 on Jun. 26, 2014, the disclosure of which is hereby incorporated herein in its entirety by this reference.

TECHNICAL FIELD

This disclosure relates to restorative dentistry and especially to the field of aesthetic dentistry.

BACKGROUND

Dental veneers are wafer-thin, custom-made shells of tooth-colored materials designed to cover the front surface of teeth to improve their appearance or to cover damaged tooth surfaces. These shells are bonded to the front of the teeth, changing their color, shape, size, or length.

Dental veneers can be made from porcelain or from resin composite materials.

Application of porcelain veneers requires two appointments. At the first visit, the dentist will prepare each tooth by removing a minimum of approximately 0.5 millimeter of enamel from the tooth surface. Once the teeth have been prepared, the typical procedure is to take an impression of the teeth and send it to a laboratory to fabricate a custom fit product from porcelain material. At the second visit, the final product will be ready to be placed. In the meantime, the dentist will place temporary veneers over the prepared teeth.

Application of composite veneers requires a single appointment only. Composite veneers can be made thinner than porcelain and, therefore, require no, or minimal, removal of the tooth surface before the veneer is bonded to the tooth. As such, the use of composite veneers is a more conservative treatment. It is also more cost effective for the patient since there are no lab costs, less chair time, and no temporary veneers are required.

A significant drawback of directly applied composite veneers is that it can be difficult to create the precise tooth contour (line angles, grooves, and lobes) and then polish the veneer to obtain a glazed appearance, which will accurately mimic the glaze of a natural tooth. An artistic hand is required in order to produce natural seamless results and, for most dentists, a direct anterior composite veneer restoration is one of the most challenging clinical procedures. Therefore, many dentists choose to have porcelain veneers fabricated off-site by a dental laboratory, which are then bonded to the patient's tooth during a follow-up visit to the clinic.

BRIEF SUMMARY

Embodiments of this disclosure provide a template for forming a veneer on a tooth using a composite resin material that is curable by radiation (e.g., via photopolymerization) or any other dental curing light radiation (e.g., from a quartz-halogen source, a light-emitting diode (LED) source, a plasma arc source, or any other suitable type of photopolymerization radiation). The template includes a tooth-contacting portion having a smooth concave surface for contacting the composite, the smooth concave surface having a shape that is complementary to a desired natural tooth shape. The tooth-contacting portion is formed of a material capable of transmitting the radiation such that the composite is curable through the tooth-contacting portion to form a veneer having a surface shape that conforms to the desired natural tooth shape.

Other embodiments provide a kit for forming veneers using a composite that is curable by radiation (e.g., UV light or any other dental curing light radiation), the kit including a plurality of templates as described above. Respective templates have respective tooth-contacting portions having different respective predetermined shapes, such that the respective templates can accommodate variations in shape and/or size of the facial surfaces of, for example, each of the anterior teeth and first premolars within a set of teeth. The relative dimensions of respective tooth-contacting portions may be determined on a theoretical basis, for example, using the golden proportions theory of Levin, the Snow proportion, or any other proportions derived from aesthetic smile analysis. Alternatively, the relative dimensions may be determined on an empirical basis, for example, from measured values of average natural tooth width and length in a given adult population.

Further embodiments provide a method of forming a veneer on a tooth using a composite that is curable by radiation or any other dental curing light radiation, the method including:

providing a template having a tooth-contacting portion, the tooth-contacting portion having a smooth concave surface, the smooth concave surface having a shape that is complementary to a desired natural tooth shape, the tooth-contacting portion being formed of a material capable of transmitting the radiation;

applying the composite (or any other direct veneer material) to the facial surface of the tooth (or applying the composite of other material into the template);

pressing the tooth-contacting portion (with the composite) toward (e.g., against) the facial surface of the tooth such that the composite contacts the smooth concave surface; and curing the composite with the radiation through the tooth-contacting portion to form a veneer having a surface shape that conforms to the desired natural tooth shape and, in some embodiments, the desired glaze of the tooth.

Advantageously, with the methods, devices and kits of embodiments of the disclosure, it is possible for dentists to consistently produce composite veneers that will be sized, shaped and contoured, and will shine, in similar fashion to a natural tooth without needing to spend time on carving and polishing, and without needing to exercise significant artistic skill.

BRIEF DESCRIPTION OF THE DRAWINGS

Embodiments of the disclosure will now be described, by way of non-limiting example only, with reference to the accompanying drawings in which.

DETAILED DESCRIPTION

Embodiments provide a dental method, apparatus, and kit for creating direct composite veneers.

Embodiments of the kits disclosed herein consist of sets of templates for creating desired final shapes of composite veneers.

The desired final shapes are chosen by a method of aesthetic smile analysis, such as the golden proportions theory of Levin (*J. Prosthet. Dent.* 1978 September; 40(3): 244-52); the golden percentage of Snow (*J. Esthet. Dent.* 1999; 11(4):177-84); the Preston proportion (J. D. Preston, "The Golden Proportion Revisited," *Journal Esthet. Dent.* 1993; 5:247-51), or "Recurring Esthetic Dental (RED) Proportion" (D. H. Ward, *J. Esthet. Restor. Dent.* 2007; 19(6): 324-37; discussion 338-39). The disclosures of each of these documents are incorporated in their entirety as if fully set forth herein.

In other embodiments, the desired final shapes may be chosen based on average measured natural tooth surface geometry (including width, length, and curvature) in a particular population. Tables 1 and 2 provide examples of average tooth width and length measurements that may be used in providing a set of templates.

TABLE 1 average dimensions of maxillary teeth

| Maxillary Teeth: | Crown Length | Crown Width | CEJ (MD) Width | CEJ (BL) Width |
|---|---|---|---|---|
| Centrals | 10.5 | 8.5 | 7.0 | 6.0 |
| Laterals | 9.0 | 6.5 | 5.0 | 5.0 |
| Canines | 10.0 | 7.5 | 5.5 | 7.0 |
| 1st Premolar | 8.5 | 7.0 | 5.0 | 8.0 |
| 2nd Premolar | 8.5 | 7.0 | 5.0 | 8.0 |
| 1st Molar | 7.5 | 10.0 | 8.0 | 10.0 |
| 2nd Molar | 7.0 | 9.0 | 7.0 | 10.0 |

TABLE 2 average dimensions of mandibular teeth

| Mandibular Teeth: | Crown Length | Crown Width | CEJ (MD) Width | CEJ (BL) Width |
|---|---|---|---|---|
| Centrals | 9.0 | 5.0 | 3.5 | 5.3 |
| Laterals | 9.5 | 5.5 | 4.0 | 5.8 |
| Canines | 11.0 | 7.0 | 5.5 | 7.0 |
| 1st Premolar | 8.5 | 7.0 | 5.0 | 6.5 |
| 2nd Premolar | 8.0 | 7.0 | 5.0 | 7.0 |
| 1st Molar | 7.5 | 11.0 | 9.0 | 9.0 |
| 2nd Molar | 7.0 | 10.5 | 8.0 | 9.0 |

The curvature of the desired final shapes may also be chosen empirically according to natural tooth curvature for the respective teeth. For example, as disclosed in *Wheeler's Dental Anatomy, Physiology and Occlusion* (7th edition, W.B. Saunders, 1993), the maxillary teeth have an average curvature of about 0.5 mm at the cervical third, and the mandibular anterior teeth typically have a curvature above the cervical line of less than 0.5 mm, and often much less.

Figure 4:
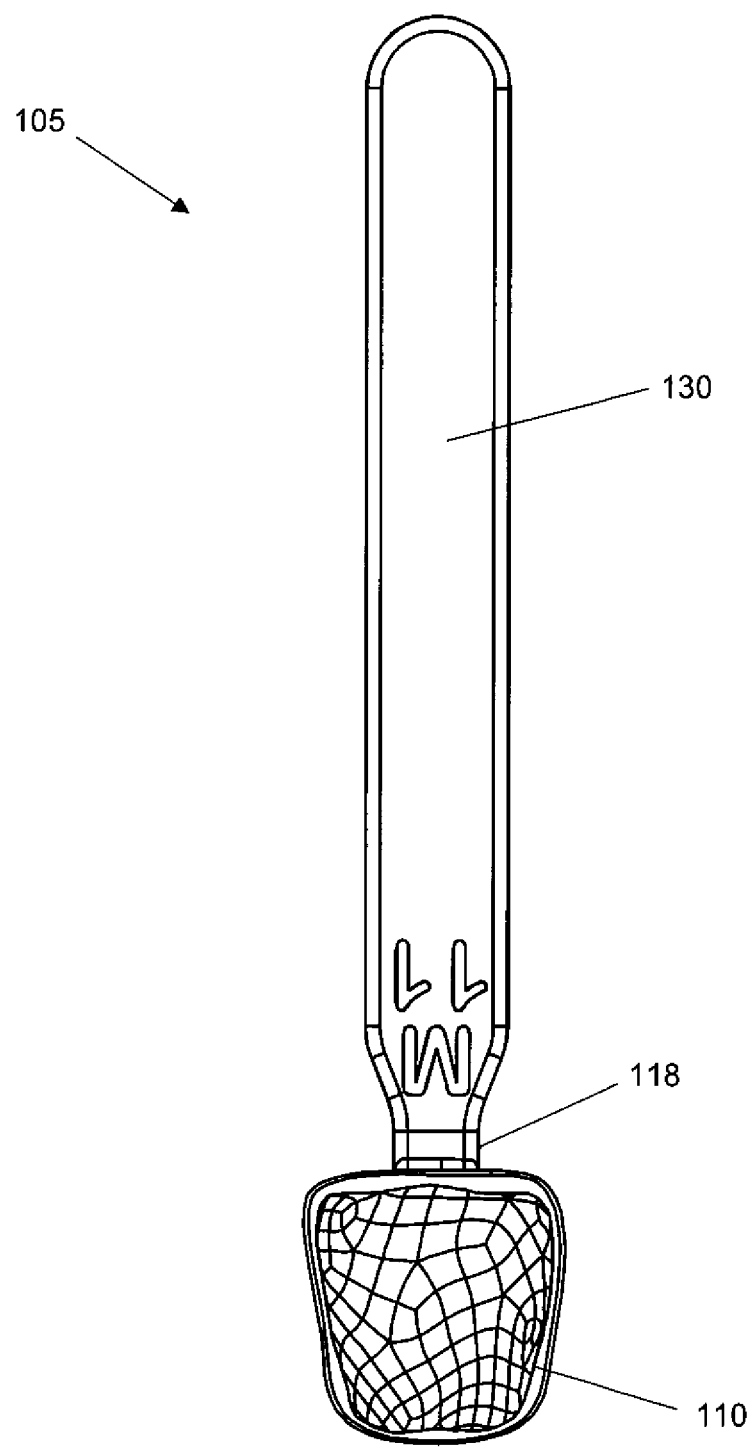
FIG. 4 is a front projection view of a removable template component used with the template of FIGS. 1 to 3.
Figure 5:
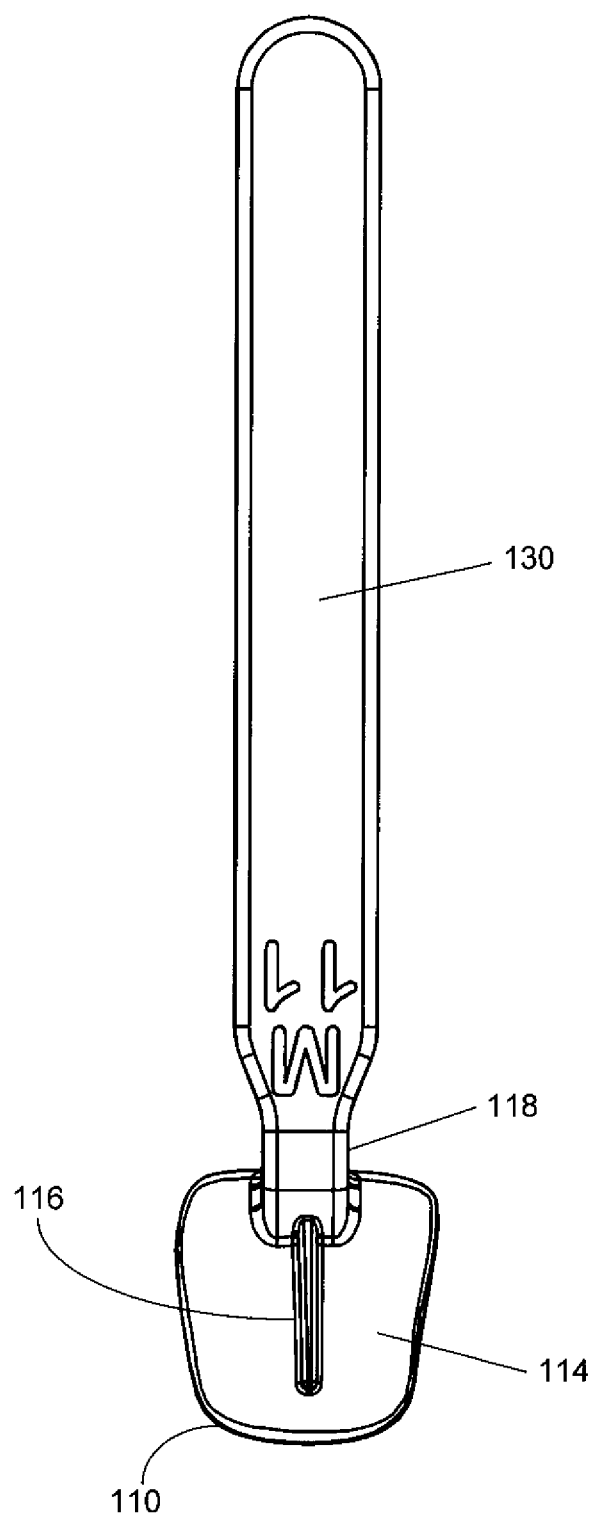
FIG. 5 is a rear plan view of the template component.
Figure 6:
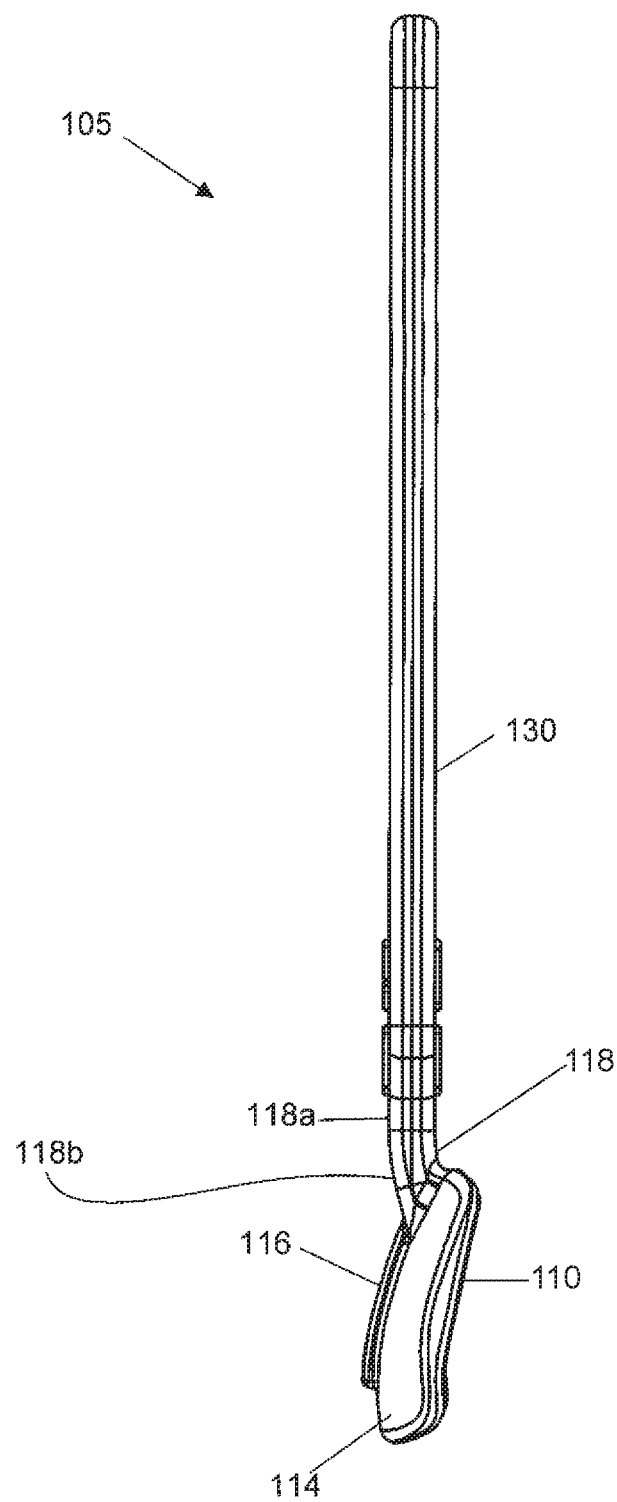
FIG. 6 is a side projection view of the template component.
Figure 7:
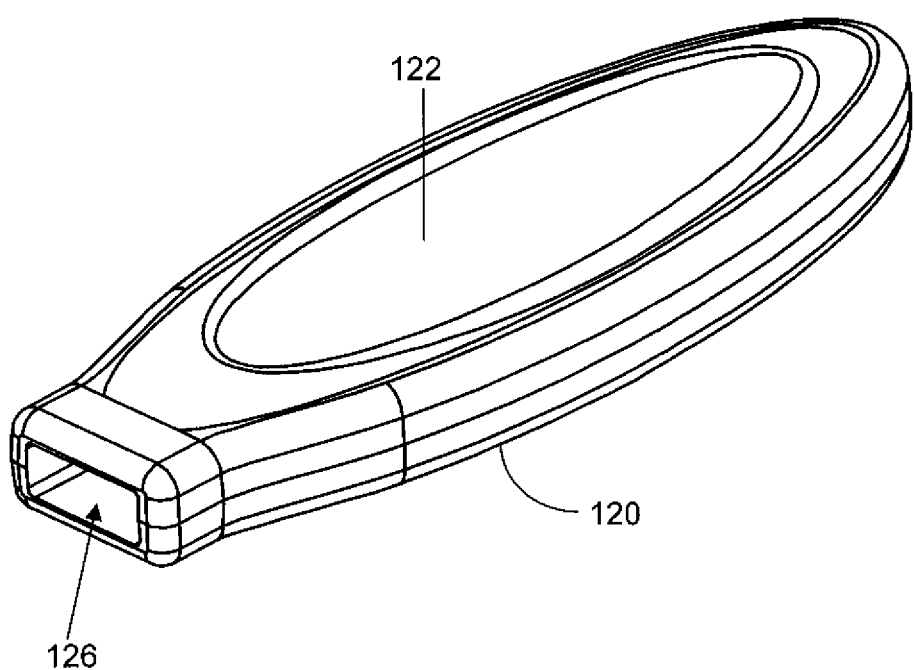
FIG. 7 is a front perspective view of a grip component of the template of FIGS. 1 and 2.

As shown in the figures, a template 100 includes a template component 105 fitted to an optional grip component 120. The template component 105 includes a tooth-contacting portion 110 with a smooth concave surface 112, which mimics the contour of a natural tooth. The tooth-contacting portion 110 extends from an elongate handle 130 (FIGS. 4 and 5). Tooth-contacting portion 110 has a surface 114, opposite smooth concave surface 112, on which is located an alignment guide 116 (FIGS. 5 and 6).

In some embodiments, the template component 105 may be used alone without the optional grip component 120. For example, a user may only use the elongate handle 130, without the optional grip component 120 to apply a veneer to a subject's tooth.

It should be appreciated that the lines shown on the surface 112 are only intended to depict curvature of the surface for illustrative purposes, and not any surface pattern or structure that might cause roughening of the surface 112.

In some embodiments, the portion of the template component 105 (e.g., the concave surface 112 of the tooth-contacting portion 110) may include a surface having a reduced coefficient of friction (e.g., a non-stick surface). Such a surface may enable the concave surface 112 of the tooth-contacting portion 110 to be easily removed from the composite material after application to a tooth, while reducing or eliminating any residue of the composite material left on the tooth-contacting portion 110. Such a surface may be formed from a polymer material, such as, for example, polytetrafluoroethylene (PTFE).

Alignment guide 116 is located along a central axis of the template component 105 and advantageously assists positioning on the midline of the tooth, and in maintaining parallelism with other reference points on the subject, such as, for example, the centerlines of adjacent teeth and/or the centerline of the subject's head or face. As shown in the drawings, the alignment guide 116 is a straight raised ridge aligned with the central axis of the template component 105, but it will be appreciated that other forms of an alignment guide are possible. For example, the alignment guide 116 may be a groove, a pair or a multiplicity of parallel raised portions and/or grooves, or may include one or more images applied by printing or another suitable method.

Template component 105 is formed from a transparent or translucent plastics material, which does not permanently adhere to dental composites.

The template component 105 is autoclavable, so that it can be reused. Advantageously, the template component 105 is formed of a flexible material, or is configured to flex at specific locations or regions, for example, along the handle 130 and/or along a portion intermediate the handle 130 and the tooth-contacting portion 110. Typically, after curing the composite, the tooth-contacting portion 110 will slightly attach to the composite. In order to remove the template, it may be necessary to apply pressure, which may cause breakage of the cured composite or of the template. Providing a flexible arm will reduce the risk of this occurring, and will distribute the forces applied to the template during disconnection.

The grip portion 120 is formed of an elastomeric material, such as silicone, and includes a recessed surface 122, which may serve as a thumb rest. The recessed surface 122 may include raised portions, for example, a series of ribs, which improve the grip of a user's thumb or finger. The raised portions may include text, such as trademarks or descriptive text.

In some embodiments, the template component 105 and grip 120 may be integrally formed.

Grip portion 120 includes a channel 126 shaped and sized to receive handle 130 of template component 105. The handle 130 may be fitted to the grip portion 120 in a number of ways, for example, by a push fit by which the material of the handle 130 frictionally engages with the elastomeric material of the grip 120, or by snap-in engagement of a groove or protrusion on the handle 130 (not shown) with a corresponding protrusion or groove located in the channel 126.

Figure 1:
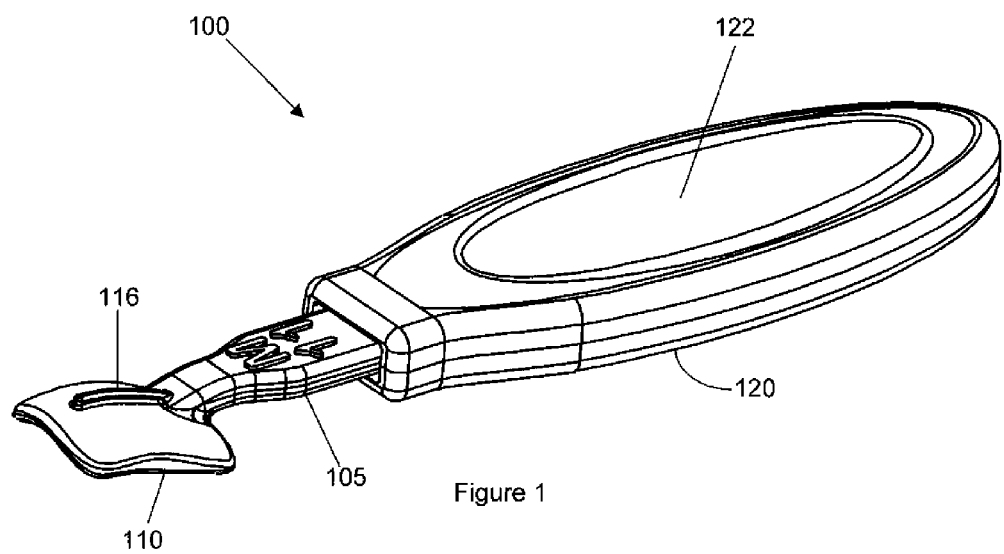
FIG. 1 is a rear perspective view of a template according to embodiments of the disclosure.
Figure 2:
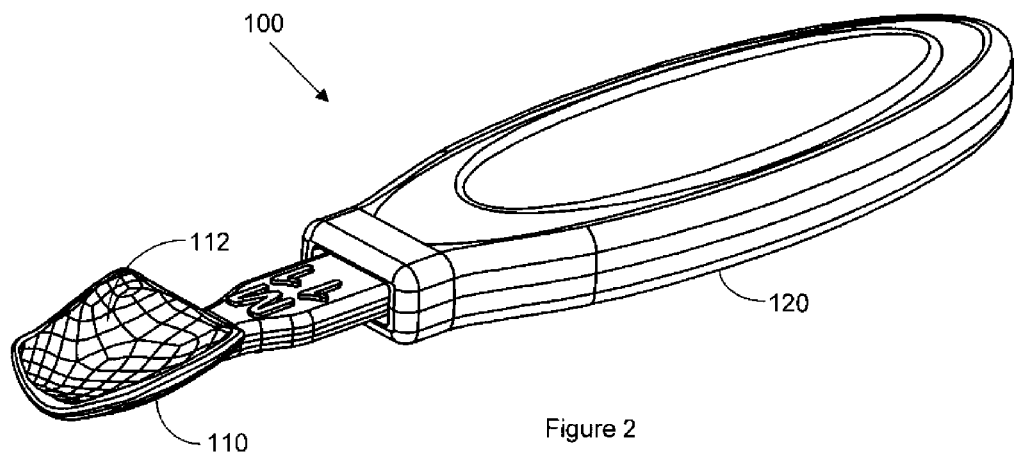
FIG. 2 is a front perspective view of the template of FIG. 1.
Figure 3:
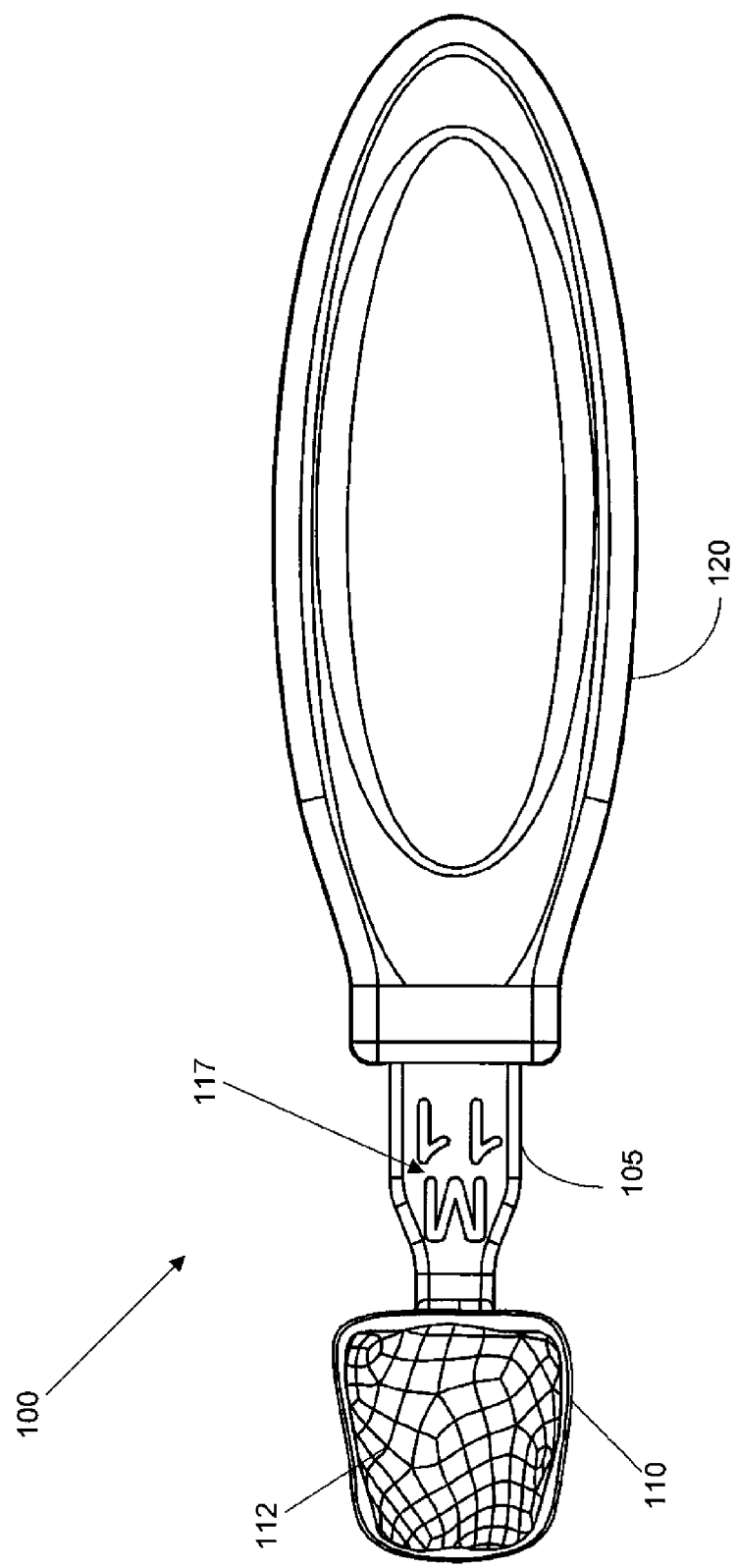
FIG. 3 is a front projection view of the template of FIGS. 1 and 2.

The smooth concave surface 112 (depicted as a series of lines to show its curvature) of the tooth-contacting portion 110 of the particular examples as shown in FIGS. 2, 3, and 4 is shaped in such a manner that it will conform to the ideal shape (including dimensions and curvature) of the labial surface of a natural tooth, in this example, a maxillary central incisor. The ideal shape can be determined by any of the methods of choosing desired tooth shapes as mentioned above. Thus, the template component 105 as particularly illustrated is suitable for application of veneers to the maxillary central incisors.

Embodiments of the disclosure provide a kit comprising a plurality of template components 105, having respective tooth-contacting portions 110 with concave surfaces 112, which have different respective shapes to accommodate variations in shape of the facial (labial or buccal) surfaces within a set of natural teeth. The various template components 105 can be fitted to grip 120 to apply a veneer, and removed from the grip 120 and autoclaved after use. Alternatively, the template components 105 may be used without grip 120, with the user instead gripping handle 130 directly.

For example, a kit that is primarily to be used for aesthetic dentistry may include a total of 16 different template components, having respective template portions shaped to accommodate the eight upper and eight lower anterior teeth from the first left premolar to the first right premolar (14-24 and 44-34, in the notation used by the FDI World Dental Federation). Further, the kit may include size variations for each tooth, to allow for variation amongst patients. For example, kits may be provided in "small," "medium" and "large" sizes to accommodate the expected range of variation. In further embodiments, the kits may include different shapes of teeth (e.g., substantially square and/or round teeth).

Template component 105 includes indicia 117 on its handle 130 to indicate the size (M for medium) and tooth (11, i.e., right maxillary central incisor) for which the template component 105 is to be used.

The tooth-contacting portion 110 is joined to the handle 130 of template component 105 by a neck 118. As shown in FIG. 6, neck 118 includes a straight portion 118a that is generally aligned with a plane of handle 130, and a curved and/or angled portion 118b intermediate the straight portion 118a and the tooth-contacting portion 110. The angled portion 118b compensates for the curvature of the surface of tooth-contacting portion 110 such that tooth-contacting portion 110 is substantially aligned with the plane of handle 130.

An exemplary method for forming a veneer on a tooth, for example, using the template components 105 and/or grips 120 described above, will now be described.

First, the dentist selects an appropriate composite material and color for the tooth being treated. The color may be chosen based on the color of the patient's adjoining teeth. In alternative embodiments, the color may not match the adjacent tooth color, in case the patient or practitioner (e.g., dentist) wants to create a set of white teeth, for example. Then the dentist chooses, from a kit of templates as described above, the template component 105 that corresponds with the tooth to be veneered. The template choice may also depend on the size of the tooth, so that, for example, one of three pre-made sizes (small, medium, large) is selected such that the tooth-contacting portion 110 covers a space beginning at the gum line and spanning the contact points of the tooth with the teeth on either side. The tooth is then separated from its neighboring teeth with matrices on each side, taking care to ensure that the matrices do not protrude onto the facial surface of the tooth to prevent interference with the placement of the template.

The tooth surface is then prepared by etching in a manner known in the art, and applying a bonding agent. Any suitable bonding agent known in the art may be used. In embodiments, where the veneer is to be applied as a mockup or a temporary veneer, no bonding stage may be required.

Next, the selected template component 105 is gripped by handle 130, or by grip portion 120 if the handle 130 is seated in a grip portion or if the template component 105 and grip 120 are integrally formed, and the smooth contoured surface 112 of tooth-contacting portion 110 is then seated and lightly pressed against the composite applied on the tooth, covering the entire tooth surface. The tooth-contacting portion 110 of the template should be seated in a way that the alignment guide 116 on the tooth-contacting portion 110 will be parallel with the centerline of the adjacent tooth. In some embodiments, the tooth-contacting portion 110 can be loaded in the middle of concave surface 112 with a very small amount of flowable composite prior to applying to the facial surface of the tooth, to thereby assist with creation of a smooth bubble-free surface.

In some embodiments, only one layer (as opposed to multiple layers as is in conventional in applying a veneer) may be applied either directly to the subject's tooth or on the tooth-contacting portion 110. In particular, the concave surface 112 of the tooth-contacting portion 110, which mimics the surface of a natural enamel, enables the final thickness of the composite on the tooth to vary in differing areas of the tooth as the tooth-contacting portion 110 is forced (e.g., pressed) toward the tooth. As a result, different shades of value (e.g., high and low value) may be created with the same single shade of composite. For example, the final thickness of the composite on the tooth may be less thick near the gingiva (i.e., gums) and near the incisal edge of the tooth while being relatively thicker in the center or middle portion of the tooth. Such an embodiment, may will result in differences in color, thereby emulating a natural tooth color effect due to different absorption of light similar to a natural enamel. Stated in another way, the concave surface 112 of the tooth-contacting portion 110 enables the use of only a single layer of composite as the concave surface 112 acts to displace or migrate the composite as the tooth-contacting portion 110 is pressed toward the tooth in order to fill the areas between the concave surface 112 and the tooth with composite (e.g., in difference thicknesses so that the final result will look like a natural tooth) and form a final veneer with only a single layer of composite.

In some embodiments, the material of the template component 105 (e.g., the concave surface 112 of the tooth-contacting portion 110) enables the dentist to utilize the tooth-contacting portion 110 to apply force to the composite material placed on a subject's tooth (e.g., while curing the composite with radiation). One problem with photocurable materials is the tendency of discontinuities (e.g., voids, bubbles, or spaces) that may be incorporated into photocurable materials prior to curing. Such discontinuities, if not removed, may result in a porous cured material that is easily stained, more likely to absorb water and break, and/or form a weaker bond between the veneer and the tooth. Such pressing force on the template may improve the consistency of the composite material used to form the veneer on the subject's tooth by reducing (e.g., eliminating) discontinuities in the composite material. For example, the template component 105 may be utilized to reduce the amount of gaps (e.g., air bubbles) in the composite material in order to create a stronger, more consistent veneer, which may be less susceptible to defects or damage, such as chipping.

Once the tooth-contacting portion 110 is in place against the facial surface of the tooth, a dental curing light is used as a light source to cure the composite, curing from facial and (optionally) inner surfaces. As known in the art, the time required for curing will generally depend on the type of light used, and the thickness of the composite layer. Typically, it is advantageous to irradiate from either side of the tooth, from the back (lingual side) and from the front (labial side).

After the composite has been cured for the recommended time, the template component 105 is then removed, leaving a glazed, contoured veneer having the desired natural tooth shape. Advantageously, with this method, no carving, contouring or polishing of the veneer is required. The method saves time and produces predictable results each time.

Another problem with photocurable materials is the tendency for photocurable resins, to deform or shrink during curing due to the contraction of the resin. For example, U.S. Pat. No. 5,104,591 to Masuhara et al., the disclosure of which is incorporated in its entirety by this reference, attempts to address this problem by teaching an extraoral procedure involving covering a photocurable resin on a dental prosthesis with a film in a confined container then applying pressurized gas to the film simultaneously during light curing to reduce shrinkage. However, it should be appreciated that this pressurized gas apparatus cannot be used for any intraoral curing of photocurable resins. In some embodiments, the material of the template component 105 (e.g., the tooth-contacting portion 110) may press and act to reduce such polymerization shrinkage.

The polymerization of most, if not all, photocurable materials is inhibited in the presence of oxygen producing an uncured layer of material on any oxygen exposed surface of photocured materials. An oxygen inhibited layer is undesirable for many dental applications for at least two reasons, first, it results in a weaker bond and, second, it often results in a cured product with an uneven surface that causes future staining and roughness of the restoration. To prevent the formation of an oxygen-inhibited layer, an oxygen free environment must be provided. Providing an oxygen free curing environment in extraoral applications has been accomplished by photocuring in an oxygen free container like that taught in U.S. Pat. No. 5,104,591, discussed above. The oxygen free container method of photocuring is completely unsuitable for intraoral curing for obvious reasons. U.S. Pat. No. 5,415,543 to Rozmajzl, Jr., the disclosure of which is incorporated in its entirety by this reference, attempts to provide an oxygen free environment for intraoral photocuring by delivering a blanket of inert gas to an intraoral curing site thus displacing ambient oxygen and reducing the oxygen inhibited layer. However, such an approach not only adds another step and piece of equipment, but also poses risks and involves precautions that make it undesirable for intraoral use. In some embodiments, the material of the template component 105 (e.g., the tooth-contacting portion 110) may act to inhibit the amount of oxygen that is transmitted to the composite material. For example, the material of the tooth-contacting portion 110 may comprise a material (e.g., a polymer having low permeation properties) that will reduce (e.g., block) an amount of gas (e.g., oxygen) in communication with the composite material during the curing process. At least partially shielding the composite material from oxygen during the curing process with the tooth-contacting portion 110 may aid in forming a desirable glossy finish on the veneer that is similar to the glossy finish of healthy natural teeth and may produce a veneer that is relatively more color stable and less susceptible to staining.

As the tooth-contacting portion 110 is seated over the prepared tooth, a thin film of excess composite resin will be expressed into the margins of the prepared tooth. A finishing step is performed in order to remove the excess material from around the margins of the prepared tooth. The finishing step is performed just after removing the template component 105. Extra-fine finishing diamond burs are typically used to remove the excess material. Generally, it is important that the glazed, contoured facial surface of the tooth is not touched.

It will be appreciated that various modifications of the above methods and apparatus are possible while still falling within the scope of the disclosure. For example, while the template components 105 have been described with reference to their use with facial surfaces of anterior teeth, the template components could be used for other purposes, such as creating the final anterior shape of provisionals for porcelain veneers and crowns. The template components may also be used to create direct and indirect mock-ups with composites.

Templates of the instant disclosure and use thereof may provide veneers having enhanced surface quality that may minimize surface irregularities in the veneers that may enhance plaque accumulation, which in turn can lead to secondary caries and inflammation of the adjacent gingival tissues. Especially in the case of restorations, which are exposed to strong occlusal load and antagonistic activity, surface roughness affects the wear resistance and the abrasiveness of dental composites. Rough composite surfaces are liable to discoloration and staining. Moreover, material properties such as mechanical and flexural strength as well as microhardness of resin-based composites are improved by minimizing surface roughness. Thus, accomplishing a superior surface finish may enhance patient satisfaction and the longevity of a composite restoration.

Furthermore, templates of the instant disclosure may provide a single tool or device that may create the desired tooth shape for the veneer while, at the same time, removing discontinuities from the composite material and reduce an amount of gas (e.g., oxygen) in communication with the composite material during the curing process.

The reference in this specification to any prior publication (or information derived from it), or to any matter that is known, is not, and should not be taken as an acknowledgment or admission or any form of suggestion that that prior publication (or information derived from it) or known matter forms part of the common general knowledge in the field of endeavor to which this specification relates.

Throughout this specification, unless the context requires otherwise, the word "comprise," and variations such as "comprises" and "comprising," will be understood to imply the inclusion of a stated integer or step or group of integers or steps but not the exclusion of any other integer or step or group of integers or steps.

Once being apprised of the templates and related assemblies of the disclosure, one of ordinary skill in the art will be readily able to make and assemble the templates and related assemblies.

While embodiments of the disclosure may be susceptible to various modifications and alternative forms, specific embodiments have been shown by way of example in the drawings and have been described in detail herein. However, it should be understood that the disclosure is not limited to the particular forms disclosed. Rather, the disclosure encompasses all modifications, variations, combinations, and alternatives falling within the scope of the disclosure as defined by the following appended claims and their legal equivalents.

What is claimed is:

1. A template for forming a veneer on a tooth using a composite resin material that is curable by radiation, the template comprising:
    a tooth-contacting portion having a smooth concave surface for contacting the composite after the composite has been applied on the tooth, a continuous perimeter of the smooth concave surface defining edges of the tooth-contacting portion, the smooth concave surface having a shape that is complementary to a desired natural tooth shape of a specific tooth and adapted to form an uncured veneer comprising the composite resin into a surface shape that conforms to the desired natural tooth shape;
    an elongated handle fixed to the tooth-contacting portion, the elongated handle extending from the tooth-contacting portion and configured to be gripped by a user, the template further configured to flex along at least a portion of the elongated handle; and
    at least one alignment guide on a surface opposite the smooth concave surface configured to assist in at least one of aligning the template relative to the midline of a tooth or maintaining parallelism with at least one reference point on a subject;
    wherein the tooth-contacting portion is formed of a material capable of transmitting the radiation such that the composite is curable through the tooth-contacting portion to form a cured veneer having the surface shape that conforms to the desired natural tooth shape of the specific tooth, and wherein the elongated handle is configured to remove the tooth-contacting portion of the template from the tooth after curing the cured veneer.

2. The template of claim 1, wherein the alignment guide extends along a centerline of the tooth-contacting portion and is configured to assist in aligning the template with at least one of a centerline of at least one adjacent tooth or a centerline of the subject's head or face.

3. The template of claim 1, wherein the alignment guide comprises a raised portion or groove defined on the surface of the template that is opposite the smooth concave surface.

4. The template of claim 1, wherein at least a portion of the template comprises an autoclavable material.

5. The template of claim 1, wherein the template is configured to flex along at least one of the handle or a portion intermediate the elongated handle and the tooth-contacting portion, and wherein the elongated handle is secured to the tooth-contacting portion in a non-releasable manner.

6. The template of claim 5, further comprising a detachable grip portion attached to the handle.

7. The template of claim 1, wherein the smooth concave surface of the tooth-contacting portion comprises a substantially non-stick material.

8. The template of claim 1, wherein the template is formed of a resilient material.

9. The template of claim 1, wherein the shape of the smooth concave surface complementary to the desired natural tooth shape is based on an empirical basis from measured values of average natural tooth shapes and dimensions.

10. A kit for forming veneers using a composite that is curable by radiation, the kit comprising:
    a plurality of templates of claim 1;
    wherein respective templates have respective tooth-contacting portions having different respective predetermined shapes, the respective templates configured to accommodate variations in at least one of shape or size of the facial surfaces within a set of natural teeth.

11. A method of forming a veneer on a tooth using a composite that is curable by radiation, the method comprising:
    providing flail the template of claim 1;
    applying the composite to the facial surface of the tooth;
    after applying the composite to the facial surface of the tooth, pressing the tooth-contacting portion against the facial surface of the tooth such that the composite contacts the smooth concave surface; and
    curing the composite with the radiation through the tooth-contacting portion to form a veneer having a surface shape that conforms to the desired natural tooth shape.

12. The method according to claim 11, further comprising aligning the tooth-contacting portion of the template with the alignment guide extending along a centerline of the tooth-contacting portion relative to a centerline of a portion of a subject.

13. The method according to claim 11, wherein applying the composite to the facial surface of the tooth comprises utilizing only a single layer of the composite to the form the final veneer on the tooth.

14. The method according to claim 11, further comprising removing at least some discontinuities in the composite by pressing the tooth-contacting portion of the template toward the tooth.

15. The method according to claim 11, further comprising selecting the desired natural tooth shape on an empirical basis from measured values of average natural tooth shapes and dimensions.

16. A kit for forming veneers using a composite that is curable by radiation, the kit comprising:
    a plurality of templates for forming veneers using a composite that is curable by radiation, each template of the plurality of templates comprising:
        a tooth-contacting portion having a smooth concave surface for contacting the composite after the composite has been applied on the tooth, the smooth concave surface of each template having a predetermined shape that is distinct and different from the predetermined shape of the smooth concave surface of the remainder of the plurality of templates, the smooth concave surface of each template having the predetermined shape that is complementary to a desired individual natural tooth shape in order to accommodate variations in the shape and the size of the facial surfaces within a set of natural teeth, wherein a continuous perimeter of the smooth concave surface defines edges of the tooth-contacting portion;

an elongated handle fixed to the tooth-contacting portion, the elongated handle extending from the tooth-contacting portion and configured to be gripped by a user, the template further configured to flex along the elongated handle; and at least one alignment guide on a surface opposite the smooth concave surface configured to assist in at least one of aligning the template relative to the midline of a tooth or maintaining parallelism with at least one reference point on a subject.

17. A kit for forming veneers using a composite that is curable by radiation, the kit comprising:

a plurality of templates for forming veneers using a composite that is curable by radiation, each template of the plurality of templates comprising:

a tooth-contacting portion having a smooth concave surface for contacting the composite after the composite has been applied on the tooth, a continuous perimeter of the smooth concave surface defining outer boundaries of the tooth-contacting portion, the smooth concave surface of each template having a predetermined shape that is distinct and different from the predetermined shape of the smooth concave surface of the remainder of the plurality of templates, the smooth concave surface of each template having the predetermined shape that is complementary to a desired individual natural tooth shape in order to accommodate variations in the shape and the size of the facial surfaces within a set of natural teeth;

an elongated handle fixed to the tooth-contacting portion, the elongated handle extending from the tooth-contacting portion and configured to be gripped by a user, the template further configured to flex along a portion of at least one of the elongated handle or the template intermediate the elongated handle and the tooth-contacting portion; and at least one alignment guide on a surface opposite the smooth concave surface configured to assist in aligning the template relative to at least one reference point on a subject.

* * * * *

UNITED STATES PATENT AND TRADEMARK OFFICE
CERTIFICATE OF CORRECTION

PATENT NO.        : 9,855,121 B2
APPLICATION NO.   : 14/741313
DATED             : January 2, 2018
INVENTOR(S)       : Sigal Jacobson-Shagan Page 1 of 1

It is certified that error appears in the above-identified patent and that said Letters Patent is hereby corrected as shown below:

In the Claims

Claim 11, Column 10, Line 22,  change "providing flail the template"
to --providing the template--

Signed and Sealed this
Tenth Day of April, 2018

Andrei Iancu
*Director of the United States Patent and Trademark Office*